(12) United States Patent
Nakamura et al.

(10) Patent No.: US 9,029,354 B2
(45) Date of Patent: May 12, 2015

(54) FUNGICIDAL AQUEOUS SUSPENSION COMPOSITION FOR AGRICULTURE AND HORTICULTURE

(75) Inventors: Rieko Nakamura, Makinohara (JP); Tomoyuki Saiga, Odawara (JP); Satoshi Fujii, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/004,591

(22) PCT Filed: Mar. 14, 2012

(86) PCT No.: PCT/JP2012/056499
§ 371 (c)(1),
(2), (4) Date: Sep. 11, 2013

(87) PCT Pub. No.: WO2012/128135
PCT Pub. Date: Sep. 27, 2012

(65) Prior Publication Data
US 2014/0005229 A1  Jan. 2, 2014

(30) Foreign Application Priority Data
Mar. 18, 2011  (JP) ................................ 2011-061430

(51) Int. Cl.
*A01N 57/00* (2006.01)
*A01N 43/713* (2006.01)
*A01N 25/04* (2006.01)
*A01N 25/30* (2006.01)

(52) U.S. Cl.
CPC ............. *A01N 43/713* (2013.01); *A01N 25/04* (2013.01); *A01N 25/30* (2013.01)

(58) Field of Classification Search
CPC ........................... A01N 25/30; A01N 2300/00
USPC ........................................................ 514/340
See application file for complete search history.

(56) References Cited

U.S. PATENT DOCUMENTS

| | | | |
|---|---|---|---|
| 3,075,878 A * | 1/1963 | Ziffer ............................. | 424/118 |
| 4,360,526 A | 11/1982 | Zeeh et al. | |
| 2003/0050194 A1 * | 3/2003 | Hopkinson et al. ........... | 504/363 |
| 2005/0070439 A1 | 3/2005 | Kobori et al. | |
| 2007/0112069 A1 * | 5/2007 | Cho et al. ...................... | 514/534 |
| 2010/0137594 A1 | 6/2010 | Kobori et al. | |
| 2010/0292483 A1 | 11/2010 | Kobori et al. | |

FOREIGN PATENT DOCUMENTS

| | | | |
|---|---|---|---|
| DE | 3139370 A1 | 4/1983 | |
| DE | 4400451 A1 | 7/1994 | |
| EA | 000417 B1 | 6/1999 | |
| GB | 2117772 A | 10/1983 | |
| JP | WO 03016303 * | 2/2003 | ........... A01N 43/713 |
| JP | 2004-131392 * | 4/2004 | ........... A01N 43/713 |
| JP | 2004-131392 A | 4/2004 | |
| JP | 2006-143705 A | 6/2006 | |
| JP | 2009-269913 * | 11/2009 | ........... A01N 43/713 |
| JP | 2009-269913 A | 11/2009 | |
| JP | 2010-174008 A | 8/2010 | |
| JP | 2010-174009 A | 8/2010 | |
| JP | 2010-248273 * | 11/2010 | ........... A01N 43/713 |
| JP | 2010-248273 A | 11/2010 | |
| WO | WO 97/01530 A1 | 1/1997 | |
| WO | WO 03/016303 A1 | 2/2003 | |
| WO | WO 2008/140099 A1 | 11/2008 | |
| WO | WO 2009/020191 A1 | 2/2009 | |

OTHER PUBLICATIONS

Supplementary European Search Report dated Jul. 28, 2014, in EP 12760881.8.
Decision of Grant dated Jan. 13, 2015 in RU 2013141925 with partial translation.

* cited by examiner

*Primary Examiner* — Nizal Chandrakumar
(74) *Attorney, Agent, or Firm* — Foley & Lardner LLP

(57) ABSTRACT

Provided is a fungicidal aqueous suspension composition for agriculture and horticulture, comprising: a component (A) in the form of a specific oxime compound, salt thereof or N-oxide thereof, a component (B) in the form of at least one type of compound selected from the group consisting of a polyoxyalkylene alkyl ether, polyoxyalkylene fatty acid ester, polyoxyalkylene sorbitan fatty acid ester and silicone-based surfactant, and a component (C) in the form of at least one type of compound selected from the group consisting of a nonionic surfactant and anionic surfactant other than component (B).

4 Claims, No Drawings

FUNGICIDAL AQUEOUS SUSPENSION COMPOSITION FOR AGRICULTURE AND HORTICULTURE

CROSS-REFERENCE TO RELATED APPLICATIONS

This application is a National Stage application of PCT/JP2012/056499, filed Mar. 14, 2012, which claims priority from Japanese application JP 2011-061430, filed Mar. 18, 2011.

TECHNICAL FIELD

The present invention relates to a fungicidal aqueous suspension composition for agriculture and horticulture. More particularly, the present invention relates to a fungicidal aqueous suspension composition for agriculture and horticulture that contains an oxime compound and has high expected fungicidal effects even if used at a low concentration after diluting with water and without being affected by the target crop, plant disease or application method.

The present application claims priority on the basis of Japanese Patent Application No. 2011-061430 filed in Japan on Mar. 18, 2011, the contents of which are incorporated herein by reference.

BACKGROUND ART

In the cultivation of agricultural and horticultural crops, numerous agrihorticultural fungicides have been proposed for use against plant diseases. For example, Patent Documents 1 to 7 disclose a tetrazolyloxime derivative. The aforementioned patent documents state that a tetrazolyloxime derivative and an adjuvant such as a surfactant can be mixed to formulate a suspension, water-dispersible powder, liquid, oil, powder, granules or sol (flowable).

Patent Documents 1 and 5 describe nonionic surfactants in the form of polyoxyethylene alkyl ethers, polyoxyethylene alkyl esters, polyoxyethylene alkyl phenyl ethers, polyoxyethylene sorbitan alkyl esters and sorbitan alkyl esters as examples of surfactants serving as adjuvants of a tetrazolyloxime derivative.

Patent Documents 3, 4, 6 and 7 describe nonionic surfactants such as polyoxyethylene-added alkyl phenyl ethers, polyoxyethylene-added alkyl ethers, polyoxyethylene-added higher fatty acid esters, polyoxyethylene-added sorbitan higher fatty acid esters or polyoxyethylene-added tristyryl phenyl ethers as examples of surfactants serving as adjuvants of a tetrazolyloxime derivative.

In addition, Patent Document 8 describes the addition of an effect-enhancing component (c) in the form of a silicone-based surfactant, polyoxyethylene fatty acid ester or castor oil ethylene oxide adduct and the like to an agrihorticultural fungicidal composition containing a specific indole-based compound and the like.

PRIOR ART DOCUMENTS

Patent Documents

Patent Document 1: International Publication WO 03/016303
Patent Document 2: Japanese Unexamined Patent Application, First Publication No. 2004-131392
Patent Document 3: International Publication WO 08/140,099
Patent Document 4: International Publication WO 09/020,191
Patent Document 5: Japanese Unexamined Patent Application, First Publication No. 2009-269913
Patent Document 6: Japanese Unexamined Patent Application, First Publication No. 2010-174008
Patent Document 7: Japanese Unexamined Patent Application, First Publication No. 2010-174009
Patent Document 8: Japanese Unexamined Patent Application, First Publication No. 2006-143705

DISCLOSURE OF THE INVENTION

Problems to be Solved by the Invention

Agrihorticultural fungicides are required to allow the obtaining of stable fungicidal effects even if used at low concentrations at the time of use in order to minimize toxicity, environmental effects and chemical damage to crops. Oxime derivatives are compounds that demonstrate a high degree of efficacy against a wide range of plant diseases caused by oomycetes, zygomycetes, ascomycetes, basidiomycetes and deuteromycetes.

However, aqueous suspension compositions containing oxime derivatives may not always allow the obtaining of expected fungicidal effects depending on the target crop, plant disease or application method in the case of using at a low concentration after diluting with water.

Therefore, an object of the present invention is to provide a fungicidal aqueous suspension composition for agriculture and horticulture that contains an oxime derivative and constantly demonstrates high expected fungicidal effects even if used at a low concentration after diluting with water and without being affected by the target crop, plant disease or application method.

Means for Solving the Problems

The inventors of the present invention conducted extensive studies to solve the aforementioned problems. As a result, it was found that when an oxime derivative is suspended in water followed by the addition of a predetermined amount of a specific surfactant, a fungicidal aqueous suspension composition for agriculture and horticulture is obtained that constantly demonstrates high expected fungicidal effects even if used at a low concentration after diluting with water and without being affected by the target crop, plant disease or application method.

The present invention was completed as a result of conducting further studies on the basis of this finding.

Namely, the present invention includes the following.

[1] A fungicidal aqueous suspension composition for agriculture and horticulture, comprising:

component (A): an oxime compound, salt thereof or N-oxide thereof represented by formula (1):

[Chemical Formula 1]

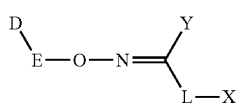

(1)

(wherein,
D represents an unsubstituted or substituted heterocyclic group,
E represents an unsubstituted or substituted C1-6 alkylene group,
L represents a single bond or an unsubstituted or substituted C1-6 alkylene group,
X represents an unsubstituted or substituted aromatic ring group or unsubstituted or substituted non-aromatic ring group, and
Y represents an unsubstituted or substituted aromatic ring group);
component (B): at least one type of compound selected from the group consisting of a polyoxyalkylene alkyl ether, polyoxyalkylene fatty acid ester, polyoxyalkylene sorbitan fatty acid ester and silicone-based surfactant; and
component (C): at least one type of compound selected from the group consisting of a nonionic surfactant and anionic surfactant other than component (B).

[2] The fungicidal aqueous suspension composition for agriculture and horticulture described in [1] above, wherein in the aforementioned formula (1), D represents either a pyridyl group represented by formula (D1):

[Chemical Formula 2]

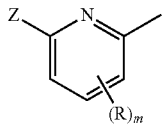

(D1)

(wherein,
R represents a halogen atom, m represents an integer of 0 to 3, R may be mutually the same or different in the case m is 2 or more, and Z represents a hydrogen atom, amino group or group represented by formula (2):
[Chemical Formula 3]

QC(=O)NH—  (2)

(wherein,
Q represents a hydrogen atom, unsubstituted or substituted C1-6 alkyl group, unsubstituted or substituted C1-6 haloalkyl group, unsubstituted or substituted C3-8 cycloalkyl group, unsubstituted or substituted C1-6 alkoxy group, unsubstituted or substituted C3-8 cycloalkyloxy group, unsubstituted or substituted benzyloxy group, unsubstituted or substituted C1-4 alkylthio group, unsubstituted or substituted C1-6 alkylamino group, unsubstituted or substituted C2-6 alkenyl group, unsubstituted or substituted aralkyl group, or unsubstituted or substituted phenyl group)], or
a thiazolyl group represented by formula (D2):

[Chemical Formula 4]

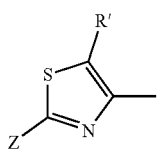

(D2)

(wherein,
R' represents a hydrogen atom or halogen atom, and Z has the same meaning as in the aforementioned formula (D1)).

[3] The fungicidal aqueous suspension composition for agriculture and horticulture described in (1) or (2) above, wherein in the aforementioned formula (1), X represents any of the groups represented by formulas (X1) to (X12):

[Chemical Formula 5]

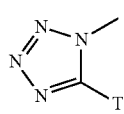 (X1)

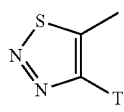 (X2)

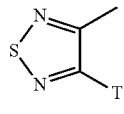 (X3)

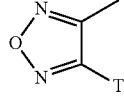 (X4)

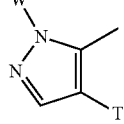 (X5)

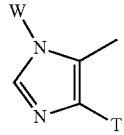 (X6)

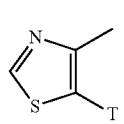 (X7)

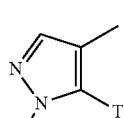 (X8)

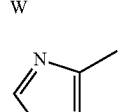 (X9)

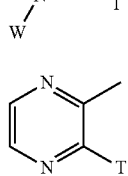 (X10)

 (X11)

-continued

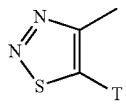
(X12)

(wherein,

T represents a hydrogen atom, unsubstituted or substituted C1-6 alkyl group, unsubstituted or substituted C2-6 alkenyl group, unsubstituted or substituted C2-6 alkynyl group, unsubstituted or substituted C3-8 cycloalkyl group, unsubstituted or substituted aryl group or unsubstituted or substituted heterocyclic group, and W represents a hydrogen atom, unsubstituted or substituted C1-6 alkyl group, unsubstituted or substituted C2-6 alkenyl group, unsubstituted or substituted C2-6 alkynyl group, unsubstituted or substituted C1-6 alkylamino group, unsubstituted or substituted C1-7 acyl group, unsubstituted or substituted C1-6 alkylcarbamoyl group or unsubstituted or substituted C1-6 alkoxycarbamoyl group).

[4] The fungicidal aqueous suspension composition for agriculture and horticulture described in any of [1] to [3] above, wherein in the aforementioned formula (1), Y represents a group represented by formula (3):

[Chemical Formula 6]

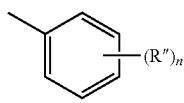
(3)

(wherein,

R" represents a halogen atom, alkyl group, alkoxy group, cyano group, methanesulfonyl group, nitro group, trifluoromethyl group or alkyl group-substituted, halogen atom-substituted or unsubstituted aryl group, n represents an integer of 0 to 5, and R" may be mutually the same or different in the case n is 2 or more).

[5] The fungicidal aqueous suspension composition for agriculture and horticulture described in any of [1] to [4] above, wherein the polyoxyalkylene alkyl ether of component (B) is a polyoxyalkylene vegetable oil ether.

[6] The fungicidal aqueous suspension composition for agriculture and horticulture described in [5] above, wherein the polyoxyalkylene vegetable oil ether of component (B) is a polyoxyethylene castor oil ether, polyoxypropylene castor oil ether or polyoxyethylene polyoxypropylene castor oil ether.

[7] The fungicidal aqueous suspension composition for agriculture and horticulture described in any of [1] to [4] above, wherein the polyoxyalkylene fatty acid ester of component (B) is a polyoxyalkylene oleic acid ester or polyoxyalkylene lauric acid ester.

[8] The fungicidal aqueous suspension composition for agriculture and horticulture described in any of [1] to [4] above, wherein the polyoxyalkylene sorbitan fatty acid ester of component (B) is a polyoxyalkylene sorbitan monooleic acid ester or polyoxyalkylene sorbitan monolauric acid ester.

[9] The fungicidal aqueous suspension composition for agriculture and horticulture described in any of [1] to [4] above, wherein the silicone-based surfactant of component (B) is a polyoxyalkylene-modified polysiloxane.

[10] The fungicidal aqueous suspension composition for agriculture and horticulture described in any of [1] to [9] above, wherein the content of component (A) is in an amount of 1% to 50% by weight, the content of component (B) is in an amount of 1% to 20% by weight, and the content weight ratio of component (A) to component (B) ((A):(B)) is 3:1 to 1:5.

[11] The fungicidal aqueous suspension composition for agriculture and horticulture described in any of [1] to [10] above, wherein the application method is foliar spraying treatment, or soil drenching treatment for rice.

[12] A method for producing a fungicidal aqueous suspension composition for agriculture and horticulture, comprising:

a step for preparing:

component (A): an oxime compound, salt thereof or N-oxide thereof represented by formula (1):

[Chemical Formula 7]

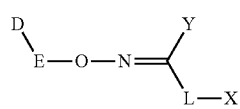
(1)

(wherein,

D represents an unsubstituted or substituted heterocyclic group,

E represents an unsubstituted or substituted C1-6 alkylene group,

L represents a single bond or an unsubstituted or substituted C1-6 alkylene group, X represents an unsubstituted or substituted aromatic ring group or unsubstituted or substituted non-aromatic ring group, and Y represents an unsubstituted or substituted aromatic ring group);

component (B): at least one type of compound selected from the group consisting of a polyoxyalkylene alkyl ether, polyoxyalkylene fatty acid ester, polyoxyalkylene sorbitan fatty acid ester and silicone-based surfactant; and component (C): at least one type of compound selected from the group consisting of a nonionic surfactant and anionic surfactant other than component (B); and a step for uniformly mixing these with water.

Effects of the Invention

The fungicidal aqueous suspension composition for agriculture and horticulture of the present invention constantly demonstrates high expected fungicidal effects even if used at a low concentration after diluting with water and without being affected by the target crop, plant disease or application method.

BEST MODE FOR CARRYING OUT THE INVENTION

Although the following provides an explanation of preferred examples of the present invention, the present invention is not limited to these examples. The constitution of the present invention can be added to, abbreviated, substituted or altered in other ways within a range that does not deviate from the gist of the present invention.

The fungicidal aqueous suspension composition for agriculture and horticulture of the present invention comprises:

component (A): an oxime compound, salt thereof or N-oxide thereof represented by formula (1):

[Chemical Formula 8]

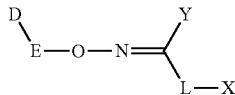

(wherein,

D represents an unsubstituted or substituted heterocyclic group,

E represents an unsubstituted or substituted C1-6 alkylene group,

L represents a single bond or an unsubstituted or substituted C1-6 alkylene group, X represents an unsubstituted or substituted aromatic ring group or unsubstituted or substituted non-aromatic ring group, and Y represents an unsubstituted or substituted aromatic ring group);

component (B): at least one type of compound selected from the group consisting of a polyoxyalkylene castor oil ether, polyoxyalkylene fatty acid ester, polyoxyalkylene sorbitan fatty acid ester and silicone-based surfactant; and component (C): at least one type of compound selected from the group consisting of a nonionic surfactant and anionic surfactant other than component (B).

The fungicidal aqueous suspension composition for agriculture and horticulture according to the present invention contains an oxime derivative, salt thereof or N-oxide thereof represented by formula (1) as component (A) (to also be referred to as Compound (1)).

Hydrates, various types of solvates and crystal polymorphisms and the like are included in Compound (1) of the present invention. Moreover, Compound (1) in the present invention includes stereoisomers based on asymmetric carbons, double bonds and the like, as well as mixtures thereof.

An explanation is first provided of the meanings of "unsubstituted" and "substituted" in formula (1).

The term "unsubstituted" refers to the aforementioned group being the only group serving as a mother nucleus. When there is no description of being "substituted" and a description is only provided for the name of the group serving as a mother nucleus, this refers to "unsubstituted" unless specifically indicated otherwise.

On the other hand, the term "substituted" refers to any hydrogen atom or a group serving as a mother nucleus being substituted with a group having a structure that is the same as or different from the mother nucleus. Thus, a "substituent" is another group substituted for a group serving as the mother nucleus. There may be one substituent or two or more substituents. Two or more substituents may be the same or may be different. For example, a substituted C1-6 alkyl group refers to an alkyl group in which the group serving as the mother nucleus has 1 to 6 carbon atoms, and any of the hydrogen atoms of the aforementioned alkyl group are substituted with a group having a different structure.

The term "C1-6", for example, indicates that the number of carbon atoms of the group serving as the mother nucleus is 1 to 6. The number of carbon atoms present in substituents is not included in this number of carbon atoms. For example, a butyl group having an ethoxy group as a substituent thereof is classified as a C2 alkoxy C4 alkyl group.

There are no particular limitations on "substituents" provided they are chemically allowed and have the effect of the present invention.

Examples of groups able to be "substituents" include:

halogen atoms such as a fluorine atom, chlorine atom, bromine atom or iodine atom;

alkyl groups such as a methyl group, ethyl group, n-propyl group, i-propyl group, n-butyl group, s-butyl group, i-butyl group, t-butyl group, n-pentyl group, n-hexyl group or n-hexyl group, and preferably C1-6 alkyl groups;

cycloalkyl groups such as a cyclopropyl group, cyclobutyl group, cyclopentyl group, cyclohexyl group or cycloheptyl group, and preferably C3-8 cycloalkyl groups;

alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or cinnamyl group, and preferably C2-6 alkenyl groups;

cycloalkenyl groups such as a 2-cyclopropenyl group, 2-cyclopentenyl group, 3-cyclohexenyl group or 4-cyclooctenyl group, and preferably C3-8 cycloalkenyl groups;

alkynyl groups such as a ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group, and preferably C2-6 alkynyl groups;

alkoxy groups such as a methoxy group, ethoxy group, n-propoxy group, i-propoxy group, n-butoxy group, s-butoxy group, i-butoxy group or t-butoxy group, and preferably C1-6 alkoxy groups;

alkenyloxy groups such as a vinyloxy group, allyloxy group, propenyloxy group or butenyloxy group, and preferably C2-6 alkenyloxy groups;

alkynyloxy groups such as a ethynyloxy group or propargyloxy group, and preferably C2-6 alkynyloxy groups;

aryl groups such as a phenyl group, 1-naphthyl group or 2-naphthyl group, and preferably C6-10 aryl groups;

aryloxy groups such as a phenoxy group or 1-naphthoxy group, and preferably C6-10 aryloxy groups;

aralkyl groups such as a benzyl group or phenethyl group, and preferably C7-11 aralkyl groups;

aralkyloxy groups such as a benzyloxy group or phenethyloxy group, and preferably C7-12 aralkyloxy groups;

acyl groups such as a formyl group, acetyl group, propionyl group, benzoyl group or cyclohexylcarbonyl group, and preferably C1-7 acyl groups;

acyloxy groups such as a formyloxy group, acetyloxy group, propionyloxy group, benzoyloxy group or cyclohexylcarbonyloxy group, and preferably C1-7 acyloxy groups;

alkoxycarbonyl groups such as a methoxycarbonyl group, ethoxycarbonyl group, n-propoxycarbonyl group, i-propoxycarbonyl group, n-butoxycarbonyl group or t-butoxycarbonyl group, and preferably C1-6 alkoxycarbonyl groups;

carboxyl group;

hydroxyl group;

haloalkyl groups such as a chloromethyl group, chloroethyl group, 1,2-dichloro-n-propyl group, 1-fluoro-n-butyl group or perfluoro-n-pentyl group, and preferably halo-C1-6 alkyl groups;

haloalkenyl groups such as a 2-chloro-1-propenyl group or 2-fluoro-1-butenyl group, and preferably halo-C2-6 alkenyl groups; haloalkynyl groups such as a 4,4-dichloro-1-butynyl group, 4-fluoro-1-pentynyl group or 5-bromo-2-pentynyl group, and preferably halo-C2-6 alkynyl groups;

haloalkoxy groups such as a 2-chloro-n-propoxy group or 2,3-dichlorobutoxy group, and preferably halo-C1-6 alkoxy groups;

haloalkenyloxy groups such as a 2-chloropropenyloxy group or 3-bromobutenyloxy group, and preferably halo-C2-6 alkenyloxy groups;

haloaryl groups such as a 4-chlorophenyl group, 4-fluorophenyl group or 2,4-dichlorophenyl group, and preferably halo-C6-10 aryl groups;

haloaryloxy groups such as a 4-fluorophenyloxy group or 4-chloro-1-napthoxy group, and preferably halo-C6-10 aryloxy groups;

halogen-substituted acyl groups such as a chloroacetyl group, trifluoroacetyl group, trichloroacetyl group or 4-chlorobenzoyl group;

cyano group; isocyano group; nitro group; isocyanato group; cyanato group; amino group;

alkylamino groups such as a methylamino group, dimethylamino group or diethylamino group;

arylamino groups such as an anilino group, naphthylamino group or anthracenylamino group;

aralkylamino groups such as a benzylamino group or phenylethylamino group;

alkylsulfonylamino groups such as methylsulfonylamino group, ethylsulfonylamino group, n-propylsulfonylamino group, i-propylsulfonylamino group, n-butylsulfonylamino group or t-butylsulfonylamino group, and preferably C1-6 alkylsulfonylamino groups;

arylsulfonylamino groups such as a phenylsulfonylamino group, and preferably C6-10 arylsulfonylamino groups;

heterocyclic sulfonylamino groups such as a piperazinylsulfonylamino group, and preferably 3- to 6-membered heterocyclic sulfonylamino groups;

acylamino groups such as a formylamino group, acetylamino group, propanoylamino group, butyrylamino group, i-propylcarbonylamino group or benzoylamino group, and preferably C1-7 acylamino groups;

alkoxycarbonylamino groups such as a methoxycarbonylamino group, ethoxycarbonylamino group, n-propoxycarbonylamino group or i-propoxycarbonylamino group, and preferably C1-6 alkoxycarbonylamino groups;

haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 1,1,1-trifluoroethylsulfonylamino group or pentafluoroethylsulfonylamino group, and preferably halo-C1-6 alkylsulfonylamino groups;

bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(i-propylsulfonyl)amino group, bis(n-butylsulfonyl)amino group or bis(t-butylsulfonyl)amino group, and preferably bis(C1-6 alkylsulfonyl)amino groups;

bis(haloalkylsulfonyl)amino groups such as a bis(fluoromethylsulfonyl)amino group, bis(chloromethylsulfonyl)amino group, bis(bromomethylsulfonyl)amino group, bis(difluoromethylsulfonyl)amino group, bis(dichloromethylsulfonyl)amino group, bis(1,1-difluoroethylsulfonyl)amino group, bis(trifluoromethylsulfonyl)amino group, bis(1,1,1-trifluoroethylsulfonyl)amino group or bis(pentafluoroethylsulfonyl)amino group, and preferably bis(halo-C1-6 alkylsulfonyl)amino groups; unsubstituted or substituted hydrazino groups such as a hydrazino group, N'-phenylhydrazino group, N'-methoxycarbonylhydrazino group, N'-acetylhydrazino group or N'-methylhydrazino group;

unsubstituted or substituted aminocarbonyl groups such as an aminocarbonyl group, dimethylaminocarbonyl group, phenylaminocarbonyl group or N-phenyl-N-methylaminocarbonyl group;

unsubstituted or substituted hydrazinocarbonyl group such as a hydrazinocarbonyl group, N'-methylhydrazinocarbonyl group or N'-phenylhydrazinocarbonyl group;

N-unsubstituted or N-substituted iminoalkyl groups such as an N-methyliminomethyl group, 1-N-phenyliminoethyl group, N-hydroxyiminomethyl group or N-methoxyiminomethyl group;

mercapto group; isothiocyanato group; thiocyanato group;

alkylthio groups such as a methylthio group, ethylthio group, n-propylthio group, i-propylthio group, n-butylthio group, i-butylthio group, s-butylthio group or t-butylthio group, and preferably C1-6 alkylthio groups;

alkenylthio groups such as a vinylthio group or alkylthio group, and preferably C2-6 alkenylthio groups;

alkynylthio groups such as an ethynylthio group or propargylthio group, and preferably C2-6 alkynylthio groups;

arylthio groups such as a phenylthio group or naphthylthio group, and preferably C6-10 arylthio groups;

heteroarylthio groups such as a 2-pyridylthio group or 3-pyridazylthio group, and preferably 5- to 6-membered heteroarylthio groups;

aralkylthio groups such as a benzylthio group or phenethylthio group, and preferably C7-10 aralkylthio groups;

alkylthiocarbonyl groups such as a methylthiocarbonyl group, ethylthiocarbonyl group, n-propylthiocarbonyl group, i-propylthiocarbonyl group, n-butylthiocarbonyl group, i-butylthiocarbonyl group, s-butylthiocarbonyl group or t-butylthiocarbonyl group, and preferably C1-6 alkylthiocarbonyl groups;

alkylsulfinyl groups such as a methylsulfinyl group, ethylsulfinyl group or t-butylsulfinyl group, and preferably C1-6 alkylsulfinyl groups;

alkenylsulfinyl groups such as an allylsulfinyl group, and preferably C2-6 alkenylsulfinyl groups:

alkynylsulfinyl groups such as a propargylsulfinyl group, and preferably C2-6 alkynylsulfinyl groups;

arylsulfinyl groups such as a phenylsulfinyl group, and preferably C6-10 arylsulfinyl groups;

heteroarylsulfinyl groups such as a 2-pyridylsulfinyl group or 3-pyridylsulfinyl group, and preferably 5- to 6-membered heteroarylsulfinyl groups;

aralkylsulfinyl groups such as a benzylsulfinyl group or phenethylsulfinyl group, and preferably C7-10 aralkylsulfinyl groups;

alkylsulfonyl groups such as a methylsulfonyl group, ethylsulfonyl group or t-butylsulfonyl group, and preferably C1-6 alkylsulfonyl groups;

alkenylsulfonyl groups such as an allylsulfonyl group, and preferably C2-6 alkenylsulfonyl groups;

alkynylsulfonyl groups such as a propargylsulfonyl group, and preferably C2-6 alkynylsulfonyl groups;

arylsulfonyl groups such as a phenylsulfonyl group, and preferably C6-10 arylsulfonyl groups;

heteroarylsulfonyl groups such as a 2-pyridylsulfonyl group or 3-pyridylsulfonyl group, and preferably 5- to 6-membered heteroarylsulfonyl groups;

aralkylsulfonyl groups such as a benzylsulfonyl group or phenethylsulfonyl group, and preferably C7-10 aralkylsulfonyl groups;

unsaturated 5-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imdazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

unsaturated 6-membered heterocyclic groups such as a pyridin-2-yl group, pyridin-3-yl group, pyridin-4-yl group, 5-chloro-pyridin-3-yl group, 3-trifluoromethyl-pyridin-2-yl group, pyridazin-3-yl group, pyridazin-4-yl group, pyradin-2-yl group, pyrimidin-2-yl group, pyrimidin-4-yl group, pyrimidin-5-yl group, 1,3,5-triazin-2-yl group or 1,2,4-triazin-3-yl group;

saturated heterocyclic groups such as a tetrahydrofuran-2-yl group, tetrahydrofuran-4-yl group, piperidin-3-yl group, pyrrolidin-2-yl group, morpholino group, piperidino group or N-methylpiperazinyl group; and heterocyclooxy groups such as a 2-pyridyloxy group or 3-oxazolyloxy group.

In addition to those previously described, examples of "substituents" include groups represented by —Si($R^2$)($R^3$)($R^4$) such as —Si(Me)$_3$, —SiPh$_3$, —Si($^c$Pr)$_3$ or —Si(Me)$_2$($^t$Bu). The aforementioned $R^2$, $R^3$ and $R^4$ respectively and independently represent a C1-6 alkyl group, C3-8 cycloalkyl group or phenyl group. Specific examples of C1-6 alkyl groups and C3-8 cycloalkyl groups are the same as previously described. In addition, these "substituents" may also have additional "substituents".

D in formula (1) represents an unsubstituted or substituted heterocyclic group. A "heterocyclic group" includes groups composed of 3- to 7-membered aromatic heterocycles, saturated heterocycles, unsaturated heterocycles or 9- to 10-membered condensed heterocycles obtained by condensing these heterocycles with a benzene ring, which contain 1 to 4 heteroatoms other than carbon atoms selected from the group consisting of nitrogen atoms, oxygen atoms and sulfur atoms as atoms composing the ring. Examples of heterocyclic groups include an aziridin-1-yl group, aziridin-2-yl group, epoxy group, tetrahydrofuran-2-yl group, tetrahydrofuran-3-yl group, pyrrolidin-1-yl group, pyrrolidin-2-yl group, pyrrolidin-3-yl group, pyrrol-1-yl group, pyrrol-2-yl group, pyrrol-3-yl group, furan-2-yl group, furan-3-yl group, thiophen-2-yl group, thiophen-3-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, 1,3,4-oxadiazol-2-yl group, 1,2,4-osadiazol-3-yl group, 1,3,4-thiadiazol-2-yl group, 1,2,4-thiadiazol-3-yl group, tetrazol-1-yl group, tetrazol-2-yl group, pyridin-2-yl group, pyridin-3-yl group, pyridin-4-yl group, pyrazin-2-yl group, pyrimidin-2-yl group, pyrimidin-4-yl group, pyrimidin-5-yl group, pyridazin-3-yl group, pyridazin-4-yl group, triazinyl group, indol-1-yl group, indol-2-yl group, indol-3-yl group, indol-4-yl group, indol-5-yl group, indol-6-yl group, indol-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, benzoimidazol-1-yl group, benzoimidazol-2-yl group, benzoimidazol-4-yl group, benzoimidazol-5-yl group, benzoxazol-2-yl group, benzoxazol-4-yl group, benzoxazol-5-yl group, benzothiazol-2-yl group, benzothiazol-4-yl group, benzothiazol-5-yl group, chromen-2-yl group, chromen-3-yl group, chromen-4-yl group, chromen-5-yl group, chromen-6-yl group, chromen-7-yl group, chromen-8-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, piperidin-1-yl group, piperidin-2-yl group, piperidin-3-yl group, piperidin-4-yl group, piperazin-1-yl group, piperazin-2-yl group, piperazin-3-yl group, morpholin-2-yl group, morpholin-3-yl group, morpholin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group and 2,3-dihydrobenzofuran-7-yl group. Among these, 5- to 10-membered heterocyclic groups are preferable, and 5- or 6-membered aromatic heterocyclic groups are more preferable.

In formula (1), D is more preferably either a pyridyl group represented by formula (D1):

[Chemical Formula 9]

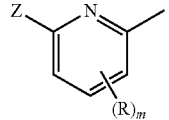

(D1)

(wherein,

R represents a halogen atom, m represents an integer of 0 to 3, R may be mutually the same or different in the case m is 2 more, and Z represents a hydrogen atom, amino group or group represented by formula (2):

[Chemical Formula 10]

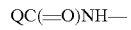

(2)

(wherein,

Q represents a hydrogen atom, unsubstituted or substituted C1-6 alkyl group, unsubstituted or substituted C1-6 haloalkyl group, unsubstituted or substituted C3-8 cycloalkyl group, unsubstituted or substituted C1-6 alkoxy group, unsubstituted or substituted C3-8 cycloalkyloxy group, unsubstituted or substituted benzyloxy group, unsubstituted or substituted C1-4 alkylthio group, unsubstituted or substituted C1-6 alkylamino group, unsubstituted or substituted C2-6 alkenyl group, unsubstituted or substituted aralkyl group or unsubstituted or substituted phenyl group)], or a thiazolyl group represented by formula (D2):

[Chemical Formula 11]

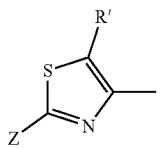
(D2)

(wherein,

R' represents a hydrogen atom or halogen atom, and Z has the same meaning as in the aforementioned formula (D1)), is even more preferably a pyridyl group represented by the aforementioned formula (D1), and in formula (D1), Z is particularly preferably a group represented by the aforementioned formula (2).

E in formula (1) represents an unsubstituted or substituted C1-6 alkylene group.

A "C1-6 alkylene group" is a linear or branched divalent hydrocarbon group. Specific examples include a methylene group, ethylene group, propylene group, butylene group, pentylene group and hexylene group.

E is more preferably an unsubstituted methylene group.

L in formula (1) represents a single bond or an unsubstituted or substituted C1-6 alkylene group.

Specific examples of a "C1-6 alkylene group" are the same as specific examples of the aforementioned E.

L is more preferably a single bond.

X in formula (1) represents an unsubstituted or substituted aromatic ring group or unsubstituted or substituted non-aromatic ring group.

Specific examples of the aforementioned aromatic ring group include aromatic hydrocarbon groups such as a phenyl group, naphthalen-1-yl group or naphthalen-2-yl group; and, aromatic heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pryazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group, pyridin-2-yl group, pyridin-3-yl group, pyridin-4-yl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group or 1,2,4-triazin-3-yl group.

Non-aromatic ring groups include all rings other than aromatic rings, and are monovalent groups obtained by eliminating any single hydrogen atom directly bonded to a ring within a non-aromatic hydrocarbon cyclic compound or non-aromatic heterocyclic compound.

Examples of non-aromatic ring groups include cycloalkyl groups such as a cyclopropyl group, cyclobutyl group, cyclopentyl group, cyclohexyl group or cycloheptyl group; cycloalkenyl groups such as a 2-cyclopropenyl group, 2-cyclopentenyl group, 3-cyclohexenyl group or 4-cyclooctenyl group; and, non-aromatic heterocyclic groups.

Non-aromatic heterocyclic groups may be monocyclic or polycyclic.

Examples of non-aromatic heterocyclic groups include an aziridin-1-yl group, aziridin-2-yl group, epoxy group, pyrrolidin-1-yl group, pyrrolidin-2-yl group, pyrrolidin-3-yl group, tetrahydrofuran-2-yl group, tetrahydrofuran-3-yl group, piperidin-1-yl group, piperidin-2-yl group, piperidin-3-yl group, piperidin-4-yl group, piperazin-1-yl group, piperazin-2-yl group, morpholin-2-yl group, morpholin-3-yl group, morpholin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group and 2,3-dihydrobenzofuran-7-yl group.

X is preferably a group represented by any of formulas (X1) to (X12):

[Chemical Formula 12]

(X1)

(X2)

(X3)

(X4)

(X5)

(X6)

(X7)

(X8)

-continued

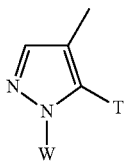

(X9)

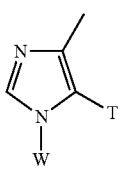

(X10)

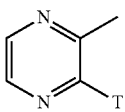

(X11)

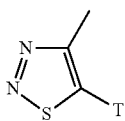

(X12)

(wherein,

T represents a hydrogen atom, unsubstituted or substituted C1-6 alkyl group, unsubstituted or substituted C2-6 alkenyl group, unsubstituted or substituted C2-6 alkynyl group, unsubstituted or substituted C3-8 cycloalkyl group, unsubstituted or substituted aryl group or unsubstituted or substituted heterocyclic group, and W represents a hydrogen atom, unsubstituted or substituted C1-6 alkyl group, unsubstituted or substituted C2-6 alkenyl group, unsubstituted or substituted C2-6 alkynyl group, unsubstituted or substituted C1-6 alkylamino group, unsubstituted or substituted C1-7 acyl group, unsubstituted or substituted C1-6 alkylcarbamoyl group or unsubstituted or substituted C1-6 alkoxycarbamoyl group).

X is more preferably a substituted tetrazol group represented by either aforementioned formula (X1) or formula (X2), and is particularly preferably a substituted tetrazol group represented by formula (X1).

Y in formula (1) represents an unsubstituted or substituted aromatic ring group.

Specific examples of the aforementioned aromatic ring are the same as specific examples of aromatic ring groups of X.

Y is preferably an unsubstituted or substituted phenyl group, and is more preferably a group represented by formula (3):

[Chemical Formula 13]

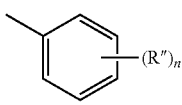

(3)

(wherein,

R" represents a halogen atom, alkyl group, alkoxy group, cyano group, methanesulfonyl group, nitro group, trifluoromethyl group or an unsubstituted or alkyl group- or halogen atom-substituted aryl group, n represents an integer of 0 to 5, and R" may be mutually the same or different in the case n is 2 or more).

Examples of salts of the aforementioned oxime compound represented by formula (1) includes salts of inorganic acids such as hydrochlorides, nitrates, sulfates or phosphates; and, salts of organic acids such as acetates, lactates, propionates or benzoates.

Examples of N-oxides of the aforementioned oxime compound represented by formula (1) include compounds in which a nitrogen atom of an oxime moiety has been oxidized, and compounds in which a nitrogen atom of a cyclic structural moiety represented by D, X or Y in formula (1) has been oxidized.

Component (A) is most preferably tert-butyl {6-{[(Z)-(1-methyl-1H-5-tetrazolyl)phenylmethylene]aminooxymethyl}-2-pyridyl}carbamate. Tert-butyl {6-{[(Z)-(1-methyl-1H-5-tetrazolyl)phenylmethylene]aminooxymethyl}-2-pyridyl}carbamate is a compound known to be an agrihorticultural fungicide.

In the present invention, component (A) may be used alone or two or more types may be used in combination. The physical properties of the component (A) used in the present invention are preferably such that the solubility thereof in water at 20° C. is 100 ppm or less, and the melting point thereof is preferably 100° C. or higher.

The content of component (A) contained in the fungicidal aqueous suspension composition for agriculture and horticulture of the present invention is preferably in an amount of 1% to 50% by weight, more preferably in an amount of 3% to 20% by weight, and even more preferably in an amount of 5% to 15% by weight.

Component (B) is at least one type of compound selected from the group consisting of a polyoxyalkylene alkyl ether, polyoxyalkylene fatty acid ester, polyoxyalkylene sorbitan fatty acid ester and silicone-based surfactant.

Examples of the polyoxyalkylene alkyl ether of component (B) include polyoxyalkylene alkyl ethers and polyoxyalkylene vegetable oil ethers in which the alkyl moiety is composed of a C8-18 linear or branched chain. Among these, polyoxyethylene vegetable oil ethers, polyoxypropylene vegetable oil ethers and polyoxyethylene polyoxypropylene vegetable oil ethers are preferable, polyoxyethylene castor oil ether, polyoxypropylene castor oil ether and polyoxyethylene polyoxypropylene castor oil ether are more preferable, and polyoxyethylene castor oil ether is even more preferable.

The polyoxyalkylene fatty acid ester of component (B) is preferably a polyoxyalkylene fatty acid ester in which the fatty acid moiety is a saturated or unsaturated fatty acid having a C8-18 linear or branched chain, a polyoxyethylene fatty acid ester or polyoxypropylene fatty acid ester is more preferable, and preferable examples thereof include polyoxyethylene oleic acid ester, polyoxyethylene lauric acid ester, polyoxyethylene palmitic acid ester, polyoxyethylene stearic acid ester and polyoxyethylene polyoxypropylene oleic acid ester. Among these, polyoxyethylene oleic acid ester or polyoxyethylene lauric acid ester is most preferable.

The polyoxyalkylene sorbitan fatty acid ester of component (B) is preferably a polyoxyalkylene sorbitan fatty acid ester in which the fatty acid moiety is a saturated or unsaturated fatty acid having one to three C8-18 linear or branched chains, a polyoxyethylene sorbitan fatty acid ester is more preferable, and preferable examples thereof include polyoxyethylene sorbitan monooleic acid ester, polyoxyethylene sorbitan monolauric acid ester, polyoxyethylene sorbitan monopalmitic acid ester, polyoxyethylene sorbitan monostearic acid ester, polyoxyethylene sorbitan dipalmitic acid ester, polyoxyethylene sorbitan distearic acid ester, polyoxyethylene sorbitan dioleic acid ester, polyoxyethylene sorbitan dilauric acid ester, polyoxyethylene sorbitan trioleic acid ester and polyoxyethylene sorbitan tristearic acid ester. Among these, polyoxyethylene sorbitan monooleic acid ester or polyoxyethylene sorbitan monolauric acid ester is most preferable.

The silicone-based surfactant of component (B) is preferably a surfactant having a polyorganosiloxane as a hydrophobic group. More specifically, a polyether-modified polysiloxane, obtained by adding a polyoxyalkylene to an alkyl hydrogen siloxane or by further etherifying or esterifying a terminal hydroxyl group with an alkyl group, aralkyl group or alkenyl group, or an amino polyether-modified polysiloxane, epoxy polyether-modified polysiloxane or carboxy polyether-modified polysiloxane, obtained by adding an amino group, epoxy group and/or carboxyl group thereto, is preferable. The polyorganosiloxane moiety is preferably polymethylsiloxane or polydimethylsiloxane. The aforementioned polyoxyalkylene moiety is preferably polyethylene oxide and/or polypropylene oxide. In the present invention, silicone-based surfactants available commercially under the trade names of, for example, Sylgard® series (Dow Corning Toray Co., Ltd.), Silwet® series (Momentive Performance Materials Inc.), Silicone Oil KF series (Shin-Etsu Chemical Co., Ltd.), Kinetic (Helena Chemical Co.) and Siltech (Siltech Corp.), can be used preferably. Among these, polyoxyalkylene-modified polysiloxanes are preferable, polyoxyethylene-modified polysiloxanes are more preferable, and polyoxyethylene-modified heptamethyltrisiloxane is even more preferable. Polyoxyethylene-modified heptamethyltrisiloxane is available commercially under the trade names of, for example, Silwet L-77, Silwet 408, Dow Corning Q2-5211 or Dow Corning Q2-5212.

In the present invention, the aforementioned components can be used alone or two or more types can be used in combination for component (B).

The content of component (B) contained in the fungicidal aqueous suspension composition for agriculture and horticulture of the present invention is preferably in an amount of 1% to 20% by weight, more preferably in an amount of 5% to 15% by weight, and even more preferably in an amount of 7% to 15% by weight. The content weight ratio of component (A) to component (B) ((A):(B)) in the fungicidal aqueous suspension composition for agriculture and horticulture of the present invention is preferably 3:1 to 1:5, more preferably 2:1 to 1:2, and even more preferably 1.5:1 to 1:1.5.

Component (C) is at least one type of compound selected from nonionic surfactants and anionic surfactants other than component (B).

Examples of nonionic surfactants of component (C) include polyoxyethylene aryl ethers such as polyoxyethylene alkyl phenyl ether, polyoxyethylene benzyl phenyl ether, polyoxyethylene monostyryl phenyl ether, polyoxyethylene distyryl phenyl ether or polyoxyethylene tristyryl phenyl ether, sucrose fatty acid esters, polyoxyethylene sucrose fatty acid esters, sorbitan fatty acid esters, polyoxyethylene alkylene glycols and polyoxyethylene-polyoxypropylene block copolymers.

Examples of anionic surfactants of component (C) include alkyl aryl sulfonates such as sodium alkyl aryl sulfonate, calcium alkyl aryl sulfonate or ammonium alkyl aryl sulfonate, polyoxyethylene alkyl phenyl ether sulfates, polyoxyethylene alkyl phenyl ether phosphates, alkyl sulfates, polyoxyethylene alkyl ether sulfates, polyoxyethylene alkyl ether phosphates, dialkyl sulfosuccinates, alkyl naphthalene sulfonates such as sodium alkyl naphthalene sulfonate, formaldehyde polycondensates of naphthalene sulfonates, lignin sulfonates and polycarboxylates.

In the present invention, the aforementioned components can be used alone or two or more types can be used in combination for component (C).

The content of component (C) contained in the fungicidal aqueous suspension composition for agriculture and horticulture of the present invention is preferably in an amount of 10% by weight or less and more preferably in an amount of 0.5% to 6% by weight.

The fungicidal aqueous suspension composition for agriculture and horticulture of the present invention may also contain components such as a surfactant, thickener, antifoaming agent, anti-freezing agent, organic solvent, antiseptic, antioxidant, anti-crystal precipitation agent or colorant in addition to components (B) and (C) within a range that does not impair the effects of the present invention.

A cationic surfactant or amphoteric surfactant can be used as a surfactant other than components (B) and (C).

Examples of cationic surfactants include alkyl quaternary ammonium salts, alkyl amine salts and alkyl pyridinium salts.

Examples of amphoteric surfactants include alkyl betaines, aminooxides and alkyl amino acid salts.

One type of these surfactants can be used alone or two or more types can be used in combination.

The fungicidal aqueous suspension composition for agriculture and horticulture of the present invention may also contain an agrihorticultural fungicide indicated below in addition to component (A). In addition, the fungicidal aqueous suspension composition for agriculture and horticulture of the present invention may also contain an agricultural chemical active ingredient such as a herbicide, insecticide, miticide or plant growth regulator as indicated below.

<Fungicides>

Examples include captan, thiuram, ziram, zineb, maneb, mancozeb, propineb, polycarbamate, chlorothalonil, quintozene, captafol, iprodione, procymidone, fluoroimide, mepronil, flutolanil, pencycuron, oxycarboxin, fosetyl-aluminum, propamocarb, triadimefon, triadimenol, propiconazole, diclobutrazol, bitertanol, hexaconazole, myclobutanil, flusilazole, etaconazole, fluotrimazol, flutriafen, penconazole, diniconazole, cyproconazole, fenarimol, triflumizole, prochloraz, imazalil, pefurazoate, tridemorph, fenpropimorph, triforine, buthiobate, pyrifenox, anilazine, polyoxin, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentin acetate, triphenyltin hydroxide, diethofencarb, quinomethionate, binapacryl, lecithin, sodium bicarbonate, dithianon, dinocap, fenaminosulf, diclomezine, guazatine, dodine, IBP, edifenphos, mepanipyrim, ferimzone, trichlamide, metasulfocarb, fluazinam, ethoquinolac, dimethomorph, pyroquilon, tecloftalam, fthalide, phenazine oxide, thiabendazole, tricyclazole, vinclozolin, cymoxanil, cyclobutanil, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole and carpropamide.

<Herbicides>

Examples include 2,4-D, MCPA, clomeprop, dicamba, chlorotoluron, diuron, linuron, isouron, fenuron, neburon, simazine, atrazine, simetryn, prometryn, hexazinone, propazine, desmetryn, terbumeton, propanil, bromoxynil, ioxynil, pyridate, chloridazon, bentazone, chlomethoxyfen, bifenox, acifluorfen sodium salt, flumioxazin, thidiazimin, oxadiazon, sulfentrazone, pentoxazone, pyraclonil, pyrazolynate, pyrazoxyfen, benzofenap, mesotrione, isoxaflutole, isoxachlortole, amitrole, aclonifen, diflufenican, benzobicyclon, diclofop-methyl, fluazifop-butyl, alloxydim sodium salt, clethodim, sethoxydim, tralkoxydim, tepraloxydim, bensulfuron-methyl, pyrazosulfuron-ethyl, rimsulfuron, imazosulfuron, prosulfuron, flumetsulam, diclosulam, metosulfam, imazapyr, imazaquin, pyrithiobac sodium salt, bispyribac sodium salt, pyriminobac-methyl, flucarbazone, propoxycarbazone, glyphosate, glyphosate ammonium salt, glufosinate, trifluralin, pendimethalin, benfluralin, prodiamine, propham, dithiopyr, alachlor, metolachlor, pethoxamid, acetochlor, propachlor, dimethenamid, diphenamid, napropamide, mefenacet, fentrazamide, molinate, dimepiperate, cycloate, esprocarb, thiobencarb, tiocarbazil, bensulide, dalapon, asulam, DNOC, dinoseb, flupoxam, triaziflam, quinclorac, cinmethylin, dazomet, dymron, etobenzanide, oxadiclomefone and pyributicarb.

<Insecticides/Miticides>

Organic phosphorous and carbamate-based insecticides: Examples include fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos-methyl, aldicarb, methomyl, thiodicarb, carbofuran, carbosulphan, benfuracarb, furathiocarb, propoxur, BPMC, MTMC, MIPC, carbaryl, pirimicarb, ethiophencarb, phenoxycarb, cartap, thiocyclam and bensultap.

Pyrethroid-based insecticides: Examples include permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen and acrinathrin.

Benzoylurea-based and other insecticides: Examples include diflubenzuron, chlorfluazuron, hexaflumuron, triflumuron, flufenoxuron, flucycloxuron, buprofezin, pyriproxyfen, methoprene, benzoepin, diafenthiuron, imidacloprid, fipronil, nicotine sulfate, rotenone, metaldehyde, acetamiprid, chlorfenapyr, nitenpyram, thiacloprid, clothianidin, thiamethoxam, dinotefuran, indoxacarb, pymetrozine, spinosad, emamectin, pyridalyl, tebufenozide, chromafenozide, methoxyfenozide and tolfenpyrad.

Nematocides: Examples include fenamiphos, fosthiazate and cadusafos.

Miticides: Examples include chlorobenzilate, phenisobromolate, dicofol, amitraz, BPPS, benzomate, hexythiazox, fenbutatin oxide, polynactin, chinomethionate, CPCBS, tetradifon, avermectin, milbemectin, clofentezine, cyhexatin, pyridaben, fenpyroximate, tebufenpyrad, pyrimidifen, fenothiocarb, dienochlor, fluacrypyrim, acequinocyl, bifenazate, etoxazole, spirodiclofen and fenazaquin.

Plant growth regulators: Examples include gibberellins (including gibberellin A3, gibberellin A4 and gibberellin A7), IAA and NAA.

The fungicidal aqueous suspension composition for agriculture and horticulture can be produced by uniformly mixing component (A), component (B) and a portion or all of other components with water followed by wet milling, adding water and remaining components as necessary, and mixing uniformly. Other methods may naturally also be used.

The fungicidal aqueous suspension composition for agriculture and horticulture of the present invention is suitable for application to plants (by foliar spraying), application to soil in which plants are growing (soil application), application to field surface water (water surface application) or application to seeds (seed treatment) and the like.

The fungicidal aqueous suspension composition for agriculture and horticulture of the present invention is preferably used by diluting to a low concentration with water. Although varying according to the target crop, plant disease or usage method, dilution with water is preferably carried out to a concentration of component (A) of 1 ppm to 10000 ppm and more preferably to 10 ppm to 1000 ppm.

In the case of using to foliar spraying, the fungicidal aqueous suspension composition for agriculture and horticulture that has been diluted to a low concentration with water as described above is preferably sprayed at the rate of 10 liters to 300 liters per 10 ares, and more preferably at the rate of 10 liters to 100 liters per 10 ares.

In the case of using by applying to soil or applying to a water surface and the like, the fungicidal aqueous suspension composition for agriculture and horticulture that has been diluted to a low concentration with water as described above is preferably sprayed at 0.1 g to 1000 g of component (A) per 10 ares, and more preferably at 10 g to 100 g of component (A) per 10 ares.

In the case of using to treat seeds, the fungicidal aqueous suspension composition for agriculture and horticulture that has been diluted to a low concentration with water as described above is preferably sprayed at 0.001 g to 50 g of component (A) per 1 kg of seeds.

Among these application methods, foliar spraying treatment, and soil drenching treatment for rice are particularly preferable.

The fungicidal aqueous suspension composition for agriculture and horticulture of the present invention demonstrates superior fungicidal effects against a wide range of types of filamentous fungi, including fungi belonging to oomycetes, ascomycetes, deuteromycetes and basidiomycetes.

The fungicidal aqueous suspension composition for agriculture and horticulture of the present invention constantly demonstrates high expected fungicidal effects for the control of various plant diseases occurring when cultivating agrihorticultural crops, including flowering plants, grasses and pasture grasses, by seed treatment, foliar spraying, soil application, water surface application, or the like, even if used at a low concentration after diluting with water and without being affected by the target crop, plant disease or application method.

The following lists examples of microorganisms that cause plant diseases against which the fungicidal aqueous suspension composition for agriculture and horticulture of the present invention demonstrates superior fungicidal effects.

Sugar beets: Cercospora leaf spot (*Cercospora beticola*)
    Aphanomyces root rot (*Aphanomyces cochlioides*)
Peanuts:
    Brown leaf spot (*Mycosphaerella arachidis*)
    Leaf spot (*Mycosphaerella berkeleyi*)
Cucumbers:
    Powdery mildew (*Sphaerotheca fuliginea*)
    Gummy stem blight (*Mycosphaerella melonis*)
    Sclerotinia rot (*Sclerotinia sclerotiorum*)
    Gray mold (*Botrytis cinerea*)
    Scab (*Cladosporium cucumerinum*)
    Downy mildew (*Pseudoperonospora cubensis*)
Tomatoes:
    Gray mold (*Botrytis cinerea*)
    Leaf mold (*Cladosporium fulvum*)

Root rot (*Pythium aphanidermatum*)
Late blight (*Phytophthora infestans*)
Eggplants:
   Gray mold (*Botrytis cinerea*)
   Black rot (*Corynespora malongenae*)
   Powdery mildew (*Erysiphe cichoracearum*)
Spinach:
   Damping-off (*Pythium ultimum*)
Strawberries:
   Gray mold (*Botrytis cinerea*)
   Powdery mildew (*Sphaerotheca aphanis*)
Onions:
   Neck rot (*Botrytis allii*)
   Gray mold (*Botrytis cinerea*)
Kidney beans:
   Stem rot (*Sclerotinia sclerotiorum*)
   Gray mold (*Botrytis cinerea*)
Apples:
   Powdery mildew (*Podosphaera leucotricha*)
   Scab (*Venturia inaequalis*)
   Blossom blight (*Monilinia mali*)
Persimmons:
   Powdery mildew (*Phyllactinia kakicola*)
   Anthracnose (*Gloeosporium kaki*)
   Angular leaf spot (*Cercospora kaki*)
Peaches/Chemies:
   Brown rot (*Monilinia fructicola*)
Grapes:
   Gray mold (*Botrytis cinerea*)
   Powdery mildew (*Uncinula necator*)
   Ripe rot (*Glomerella cingulata*)
   Downy mildew (*Plasmopara viticola*)
Pears:
   Scab (*Venturia nashicola*)
   Rust (*Gymnosporangium asiaticum*)
   Black spot (*Alternaria kikuchiana*)
Tea:
   Gray blight (*Pestalotia theae*)
   Anthracnose (*Colletotrichum theae-sinensis*)
Citrus fruit:
   Scab (*Elsinoe fawcetti*)
   Blue mold (*Penicillium italicum*)
   Common green mold (*Penicillium digitatum*)
   Gray mold (*Botrytis cinerea*)
Barley:
   Powdery mildew (*Erysiphe graminis* f. sp. *hordei*)
   Loose smut (*Ustilago nuda*)
Wheat:
   *Fusarium* blight (*Gibberella zeae*)
   Leaf rust (*Puccinia recondita*)
   Spot blotch (*Cochliobolus sativus*)
   Glume blotch (*Leptosphaeria nodorum*)
   Eye spot (*Pseudocercosporella herpotrichoides*)
   Powdery mildew (*Erysiphe graminis* f. sp. *tritici*)
   Snow mold (*Micronectriella nivalis*)
   Browning root rot (*Pythium iwayamai*)
Rice:
   Blast (*Pyricularia oryzae*)
   Sheath blight (*Rhizoctonia solani*)
   Bakanae disease (*Gibberella fujikuroi*)
   Brown spot (*Cochliobolus miyabeanus*)
   Seedling blight (*Pythium graminicola*)
Soybeans:
   Purple stain (*Cercospora kikuchii*)
   Downy mildew (*Peronospora manshurica*)
   *Phytophthora* root and stem rot (*Phytophthora sojae*)
Potatoes:
   Late blight (*Phytophthora infestans*)
Cruciferous plants:
   Clubroot (*Plasmodiophora brassicae*)
Tobacco:
   *Sclerotinia* stem-rot (*Sclerotinia sclerotiorum*)
   Powdery mildew (*Erysiphe cichoracearum*)
Tulips:
   Gray mold (*Botrytis cinerea*)
Bent grass:
   *Sclerotinia* snow blight (*Sclerotinia borealis*)
   *Pythium* red blight (*Pythium aphanidermatum*)
Orchard grass:
   Powdery mildew (*Erysiphe graminis*)

In addition, various types of pathogenic microorganisms have recently developed resistance to phenylamide-based fungicides, strobilurin-based fungicides and the like, thereby causing a lack of efficacy of these fungicides. The fungicidal aqueous suspension composition for agriculture and horticulture of the present invention is able to demonstrate superior fungicidal effects against these resistant pathogenic microorganisms as well even at low concentrations after diluting with water.

EXAMPLES

The following provides a more detailed explanation of the present invention by indicating examples thereof. However, the present invention is not limited in any way by the following examples.

In the following explanations, tert-butyl {6-{[(Z)-(1-methyl-1H-5-tetrazolyl)phenylmethylene]aminooxymethyl}-2-pyridyl}carbamate is denoted by component (A). In addition, polyoxyethylene is denoted as POE. Parts indicate parts by weight.

Example 1

10.85 parts of component (A), 0.5 parts of a 70% by weight aqueous sodium dialkylsulfosuccinate solution, 2 parts of POE tristyryl phenyl ether, 0.5 parts of antifoaming agent, 0.05 parts of antiseptic and 21.1 parts of water were mixed well followed by wet milling with a bead mill using zircon beads (Eiger Mill, Eiger Japan K.K.). 5 parts of glycerin, 10 parts of POE oleic acid ester, 0.35 parts of xanthan gum, 0.15 parts of antiseptic and 49.5 parts of water were then added to the resulting milled product and mixed well to obtain a homogeneous fungicidal aqueous suspension composition for agriculture and horticulture (Preparation 1).

Example 2

A homogeneous fungicidal aqueous suspension composition for agriculture and horticulture (Preparation 2) was obtained using the same method as Example 1 with the exception of changing the 10 parts of POE oleic acid ester to 10 parts of POE lauric acid ester.

Example 3

A homogeneous fungicidal aqueous suspension composition for agriculture and horticulture (Preparation 3) was obtained using the same method as Example 1 with the exception of changing the 10 parts of POE oleic acid ester to 10 parts of POE castor oil ether.

Example 4

A homogeneous fungicidal aqueous suspension composition for agriculture and horticulture (Preparation 4) was obtained using the same method as Example 1 with the exception of changing the 10 parts of POE oleic acid ester to 10 parts of POE sorbitan monolauric acid ester.

Example 5

A homogeneous fungicidal aqueous suspension composition for agriculture and horticulture (Preparation 5) was obtained using the same method as Example 1 with the exception of changing the 10 parts of POE oleic acid ester to 10 parts of polyoxyethylene-modified heptamethyltrisiloxane.

Comparative Example 1

A homogeneous fungicidal aqueous suspension composition for agriculture and horticulture (Preparation 6) was obtained using the same method as Example 1 with the exception of changing the amount of the POE oleic acid ester to 0 parts and changing the amount of water to 59.35 parts.

Test Example 1

Tomato Late Blight Control Test

Chemical solutions were prepared by diluting Preparations 1, 2, 3 and 6 300-fold with water (concentration of component (A): 333 ppm).

Tomato seedlings (variety: Regina) were planted in pots, one plant was assigned to each group, and testing was repeated twice on each group. The aforementioned chemical solutions were sprayed onto the tomato seedlings at leaf stage 5 to 6 using an air brush at the rate of 300 liters/ha. These were designated as treated groups. Water was sprayed onto tomato seedlings at leaf stage 5 to 6 using an air brush at the rate of 300 liters/ha. These were designated as untreated groups.

On the day after spraying, the tomato seedlings were inoculated with a suspension of zoosporangia of tomato late blight (*Phytophthora infestans*) ($0.5 \times 10^4$/ml) by spraying the backs of the leaves. The seedlings were then allowed to stand undisturbed for 2 days after inoculation in the dark in a moist chamber at 20° C. The seedlings were subsequently allowed to stand undisturbed under dry conditions for 12 hours a day at 20° C.

Six days after inoculation, a control index was determined for each pot in accordance with the four levels of criteria indicated below. A larger value for control index indicates greater fungicidal effects. The results are shown in Table 1.
<Control Index>
4: Number of spots of all plants less than 25% of untreated group
3: Number of spots of all plants 25% to less than 50% of untreated group
2: Number of spots of all plants 50% to less than 75% of Untreated group
1: Number of spots of all plants 75% or more of untreated group

TABLE 1

| Chemical | Control Index |
|---|---|
| Preparation 1 | 4 |
| Preparation 2 | 4 |
| Preparation 3 | 4 |
| Preparation 6 | 3 |

Test Example 2

Tomato Late Blight Control Test

Preparations 1 and 5 were diluted 300-fold with water to prepare chemical solutions (concentration of component (A): 333 ppm). Control indices were evaluated for these chemical solutions using the same method as Test Example 1. The results are shown in Table 2.

TABLE 2

| Chemical | Control Index |
|---|---|
| Preparation 1 | 4 |
| Preparation 5 | 4 |

Test Example 3

Rice Seedling Blight Control Test

Preparations 3, 4 and 6 were respectively diluted 2000-fold with water to prepare chemical solutions (concentration of component (A): 50 ppm).

A mycelial culture of rice seedling blight pathogen (*Pythium graminicola*) that had been cultured for 7 days at 25° C. in grass seed medium was mixed with seedling soil followed by placing in nursery boxes. Approximately 100 g of rice seeds (variety: Koshihikari) were planted per nursery box as the amount of dry seed per nursery box, followed by allowing to germinate in nursery cabinets for 2 days at 30° C. The seedlings were subsequently subjected to low-temperature treatment at 4° C. under moist chamber conditions for 4 days. Following low-temperature treatment, the seedlings were irrigated with the aforementioned chemical solutions using a watering can at the rate of 1 liter per nursery box. These were designated as treated groups. In addition, seedlings were irrigated with an equal amount of water instead of irrigating with the chemical solutions using a watering can at the rate of 1 liter per nursery box. These were designated as untreated groups.

A reference test was also conducted in which seedlings were treated in the same manner as the treated groups with the exception of not mixing the mycelial culture of rice seedling blight pathogen (*Pythium graminicola*) into the soil and using an equal amount of water instead of the chemical solutions, and this was designated as an uninoculated/untreated group.

Subsequently, the seedlings were raised in a greenhouse. On day 22 after planting, a control index was determined for each nursery box in accordance with the four levels of criteria indicated below. A larger value for control index indicates greater fungicidal effects. The results are shown in Table 3.
<Control Index>
4: Number of affected seedlings in nursery box less than 20% of untreated group
3: Number of affected seedlings in nursery box 20% to less than 40% of untreated group
2: Number of affected seedlings in nursery box 40% to less than 60% of untreated group
1: Number of affected seedlings in nursery box 60% or more of untreated group

TABLE 3

| Treatment | Control Index |
|---|---|
| Preparation 3 | 4 |
| Preparation 4 | 4 |
| Preparation 6 | 3 |
| Uninoculated/Untreated | 4 |

On the basis of the above results, the fungicidal aqueous suspension composition for agriculture and horticulture of the present invention was determined to allow the obtaining of high control values.

INDUSTRIAL APPLICABILITY

An fungicidal aqueous suspension composition for agriculture and horticulture can be provided that comprises a specific oxime compound, a salt thereof or an N-oxide thereof, and constantly demonstrates high expected fungicidal effects even if used at a low concentration after diluting with water and without being affected by the target crop, plant disease or application method.

The invention claimed is:

1. A fungicidal aqueous suspension composition for agriculture and horticulture, comprising:

component (A): an oxime compound, salt thereof or N-oxide thereof represented by formula (1):

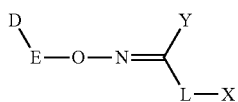
(1)

wherein,

D represents a pyridyl group represented by formula (D1):

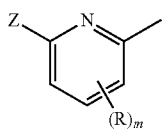
(D1)

wherein,

R represents a halogen atom, m represents an integer of 0 to 3, R may be mutually the same or different in the case m is 2 or more, and Z represents a hydrogen atom, amino group or a group represented by formula (2):

QC(=O)NH— (2)

wherein,

Q represents a hydrogen atom, unsubstituted or substituted C1-6 alkyl group, unsubstituted or substituted C1-6 haloalkyl group, unsubstituted or substituted C3-8 cycloalkyl group, unsubstituted or substituted C1-6 alkoxy group, unsubstituted or substituted C3-8 cycloalkyloxy group, unsubstituted or substituted benzyloxy group, unsubstituted or substituted C1-4 alkylthio group, unsubstituted or substituted C1-6 alkylamino group unsubstituted or substituted C2-6 alkenyl group, unsubstituted or substituted aralkyl group, or unsubstituted or substituted phenyl group, or E represents an unsubstituted or substituted C1-6 alkylene group, L represents a single bond or an unsubstituted or substituted C1-6 alkylene group, X represents any of the groups represented by formulas (X1) to (X12):

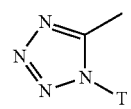
(X1)

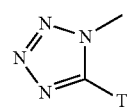
(X2)

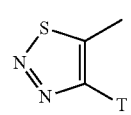
(X3)

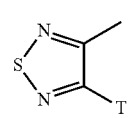
(X4)

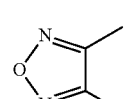
(X5)

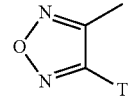
(X6)

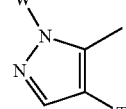
(X7)

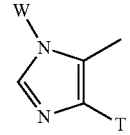
(X8)

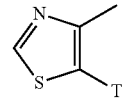
(X9)

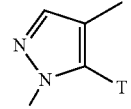
(X10)

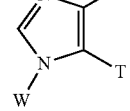
(X11)

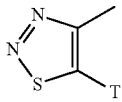
(X12)

wherein,
T represents a hydrogen atom, unsubstituted or substituted C1-6 alkyl group, unsubstituted or substituted C2-6 alkenyl group, unsubstituted or substituted C2-6 alkynyl group, unsubstituted or substituted C3-8 cycloalkyl group, unsubstituted or substituted, aryl group or unsubstituted or substituted heterocyclic group, and
W represents a hydrogen atom, unsubstituted or substituted C1-6 alkyl group, unsubstituted or substituted C2-6 alkenyl group, unsubstituted or substituted C2-6 alkynyl group, unsubstituted or substituted C1-6 alkylamino group, unsubstituted or substituted C1-7 acyl group, unsubstituted or substituted C1-6 alkylcarbamoyl group or unsubstituted or substituted C1-6 alkoxycarbamoyl group, and
Y represents a group represented by formula (3):

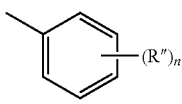
(3)

wherein,
R" represents a halogen atom, alkyl group, alkoxy group, cyano group, methanesulfonyl group, nitro group, trifluoromethyl group or alkyl group-substituted, halogen atom-substituted or unsubstituted aryl group, n represents an integer of 0 to 5, and R" may be mutually the same or different in the case n is 2 or more;
component (B): at least one type of compound selected from the group consisting of a polyoxyalkylene alkyl ether, polyoxyalkylene fatty acid ester, polyoxyalkylene sorbitan fatty acid ester and silicone-based surfactant, wherein
the polyoxyalkylene alkyl ether is a polyoxyethylene castor oil ether, polyoxypropylene castor oil ether or polyoxyethylene polyoxypropylene castor oil ether,
the polyoxyalkylene fatty acid ester is a polyoxyalkylene oleic acid ester or polyoxyalkylene lauric acid ester,
the polyoxyalkylene sorbitan fatty acid ester is a polyoxyalkylene sorbitan monooleic acid ester or polyoxyalkylene sorbitan monolauric acid ester, and
the silicone-based surfactant is a polyoxyalkylene-modified polysiloxane; and component (C): at least one type of compound selected from the group consisting of a nonionic surfactant and anionic surfactant, wherein
the nonionic surfactant of component (C) is at least one type of compound selected from the group consisting of polyoxyethylene aryl ethers, sucrose fatty acid esters, polyoxyethylene sucrose fatty acid esters, sorbitan fatty acid esters, polyoxyethylene alkylene glycols, and polyoxyethylene-polyoxypropylene block copolymers, and
the anionic surfactant of component (C) is at least one type of compound selected from the group consisting of alkyl aryl sulfonates, polyoxyethylene alkyl phenyl ether sulfates, polyoxyethylene alkyl phenyl ether phosphates, alkyl sulfates, polyoxyethylene alkyl ether sulfates, polyoxyethylene alkyl ether phosphates, dialkyl sulfosuccinates, alkyl naphthalene sulfonates, formaldehyde polycondensates of naphthalene sulfonates, lignin sulfonates, and polycarboxylates, and wherein
the fungicidal aqueous suspension composition for agriculture and horticulture is produced by the method comprising:
a step for mixing the components (A) and (C), and
a step for mixing the resultant mixture and the component (B).

2. The fungicidal aqueous suspension composition for agriculture and horticulture according to claim 1, wherein the content of component (A) is in an amount of 1% to 50% by weight, the content of component (B) is in an amount of 1% to 20% by weight, and the content weight ratio of component (A) to component (B) ((A):(B)) is 3:1 to 1:5.

3. The fungicidal aqueous suspension composition for agriculture and horticulture according to claim 1, wherein the application method is foliar spraying treatment, or soil drenching treatment for rice.

4. The fungicidal aqueous suspension composition for agriculture and horticulture according to claim 1, wherein
the amount of the component (B) contained in the fungicidal aqueous suspension composition for agriculture and horticulture is 1% to 20% by weight.

* * * * *